United States Patent [19]

Wise et al.

[11] Patent Number: 5,456,917
[45] Date of Patent: Oct. 10, 1995

[54] METHOD FOR MAKING A BIOERODIBLE MATERIAL FOR THE SUSTAINED RELEASE OF A MEDICAMENT AND THE MATERIAL MADE FROM THE METHOD

[75] Inventors: Donald L. Wise, Belmont; Debra J. Trantolo, Princeton; Joseph D. Gresser, Brookline, all of Mass.

[73] Assignee: Cambridge Scientific, Inc., Belmont, Mass.

[21] Appl. No.: 180,914

[22] Filed: Jan. 12, 1994

Related U.S. Application Data

[63] Continuation-in-part of Ser. No. 45,917, Apr. 12, 1993, abandoned.

[51] Int. Cl.⁶ .................................................. A61K 47/30
[52] U.S. Cl. ........................................ 424/426; 424/422
[58] Field of Search ............................................. 424/426

[56] References Cited

U.S. PATENT DOCUMENTS

| | | | |
|---|---|---|---|
| 3,887,699 | 6/1975 | Schacht et al. | 424/428 |
| 4,147,767 | 4/1979 | Yapel, Jr. | 424/22 |
| 4,164,560 | 8/1979 | Folkman et al. | 424/22 |
| 4,310,397 | 1/1982 | Kaetsu et al. | 204/159.22 |
| 4,348,387 | 9/1982 | Brownlee et al. | 424/178 |
| 4,357,312 | 11/1982 | Hsieh et al. | 424/15 |
| 4,450,150 | 5/1984 | Sidman | 424/1.1 |
| 4,469,681 | 9/1984 | Brownlee et al. | 424/178 |
| 4,500,337 | 2/1985 | Young et al. | 71/67 |
| 4,564,364 | 1/1986 | Zaffaroni et al. | 604/897 |
| 4,568,559 | 2/1986 | Nuwayser et al. | 427/3 |
| 4,590,062 | 5/1986 | Jang | 424/19 |
| 4,591,496 | 5/1986 | Cohen et al. | 424/15 |
| 4,623,588 | 11/1986 | Nuwayser et al. | 428/402.24 |
| 4,698,264 | 10/1987 | Steinke | 428/402.2 |
| 4,767,628 | 8/1988 | Hutchinson | 424/426 |
| 4,810,501 | 3/1989 | Ghebre-Sellassie et al. | 424/469 |
| 4,818,542 | 4/1989 | DeLuca et al. | 424/491 |
| 4,828,857 | 5/1989 | Sharma et al. | 426/285 |
| 4,837,032 | 6/1989 | Ortega | 424/469 |
| 4,897,268 | 1/1990 | Tice et al. | 424/422 |
| 4,952,402 | 8/1990 | Sparks et al. | 424/419 |
| 4,975,280 | 12/1990 | Yolles | 128/260 |
| 5,023,082 | 6/1991 | Friedman et al. | 424/426 |
| 5,039,660 | 8/1991 | Leonard et al. | 514/8 |
| 5,071,645 | 12/1991 | Johnson et al. | 424/486 |
| 5,079,005 | 1/1992 | Gupta | 424/408 |
| 5,133,755 | 7/1992 | Brekke | 623/16 |

*Primary Examiner*—Thurman K. Page
*Assistant Examiner*—Peter F. Kulkosky
*Attorney, Agent, or Firm*—Weingarten, Schurgin, Gagnebin & Hayes

[57] ABSTRACT

A method for making an implantable bioerodible material for the sustained release of a medicament and the material made from the method. The method comprises the formulation of a biomaterial polymeric carrier into particles of predetermined density and size. The particles are then are mixed with the desired medicament and extruded into the desired shape for implantation or reground to a predetermined size distribution for injection as a suspension. In an alternative embodiment, the particles of polymeric carrier are immersed in a solvent containing a medicament, and the pores of the particles are filled with medicament through alternate application and release of vacuum.

32 Claims, 3 Drawing Sheets

5,456,917

METHOD FOR MAKING A BIOERODIBLE MATERIAL FOR THE SUSTAINED RELEASE OF A MEDICAMENT AND THE MATERIAL MADE FROM THE METHOD

RELATED APPLICATION

This application is a continuation-in-part of Ser. No. 08/045,917 filed Apr. 12, 1993 now abandoned.

FIELD OF THE INVENTION

The invention relates to the field of implantable biomaterials and more specifically to implantable biomaterials for the sustained release of medicaments.

BACKGROUND OF THE INVENTION

Many medicaments are most effective when administered continuously over an extended period of time. While it has been possible to administer some of these medicaments by way of an intravenous drip or by the serial administration of the medicament either orally or hypodermically, the requisite monitoring of an intravenous drip restricts this modality to a hospital or other care intensive facility and oral or hypodermic serial administration requires either repeated visits to a healthcare provider or a strict adherence to the regimen by the patient. Examples of strict regimen therapies include those for fertility control and tuberculosis treatment. However, since many of the patients under such treatment do not have adequate access to healthcare providers, it is desirable to have a treatment modality which will minimize the number of visits to a healthcare provider while not requiring active participation on the part of the patient. To meet these goals, research in the last few years has been directed toward creating implantable sustained release implants or particles which contain the desired medicaments.

These sustained release implants or particles take on many forms. Some implants or particles are made of bioerodible polymers which release entrapped medicaments as the polymer is degraded within the body. In these devices, the rate of matrix erosion determines the rate at which the medicament is released. Other implants or particles consisting of a high porosity matrix rely on the time it takes a medicament located within the pores of the matrix to diffuse from the particle or implant.

Although sustained release implants or particles are being used in a number of different therapeutic regimens, a concern has recently arisen regarding the standard methods by which the particles or implants are fabricated. Typically polymers which form the implant or particle are dissolved in a solvent during the formation of the implant. Trace quantities of solvent may remain in the polymer during implant fabrication and patients receiving these implants or particles are exposed to the dangerous solvents which are released as the implant erodes.

The present invention relates to a solvent free method of producing bioerodible implants and particles for the administration of medicaments which permits the rate of release of the medicament to be controlled.

SUMMARY OF THE INVENTION

The invention relates to a method for making a bioerodible material for the sustained release of a medicament and the material made from the method. The method comprises adjusting the density of particles of a bioerodible material to a predetermined value and mixing the bioerodible material with the desired medicament. The resulting mixture is then extruded into forms suitable for implantation or ground into particles for such uses as inhalation delivery or hypodermic injection.

In one embodiment, the method of forming the implant comprises adjusting the density of the polymer by dissolving the erodible biomaterial in a solvent and the freeze drying of the resulting solution to form a film of bioerodible polymer of a predetermined porosity and density. The film is then removed and cryogenically ground and sieved to retain particles of a predetermined size distribution. These particles are mixed with the desired medicament and the resulting mixture is then extruded into the desired shape for implantation.

In another embodiment the method of adjusting density comprises the dissolution of the erodible biomaterial in a solvent and the precipitation of the polymer in a liquid which is miscible with the polymer solvent but in which the polymer is insoluble.

In another embodiment, the method of mixing the desired medicament and the polymer particles includes immersing the particles in a solution of medicament in which the particles are not soluble. Application of vacuum to the mixture to remove air permits the pores of the particles to be substantially completely loaded with the medicament when the vacuum is released thus forcing the solution into the pores. Subsequent freeze drying removes the solvent while retaining the medicament within the pores.

In yet another embodiment the resulting extruded bioerodible material may be reground into particles suitable for inhalation delivery or hypodermic injection.

BRIEF DESCRIPTION OF THE DRAWING

These and further features of the invention will be better understood with reference to the preferred embodiments and the drawing in which.

DESCRIPTION OF THE PREFERRED EMBODIMENT

Figure 1:
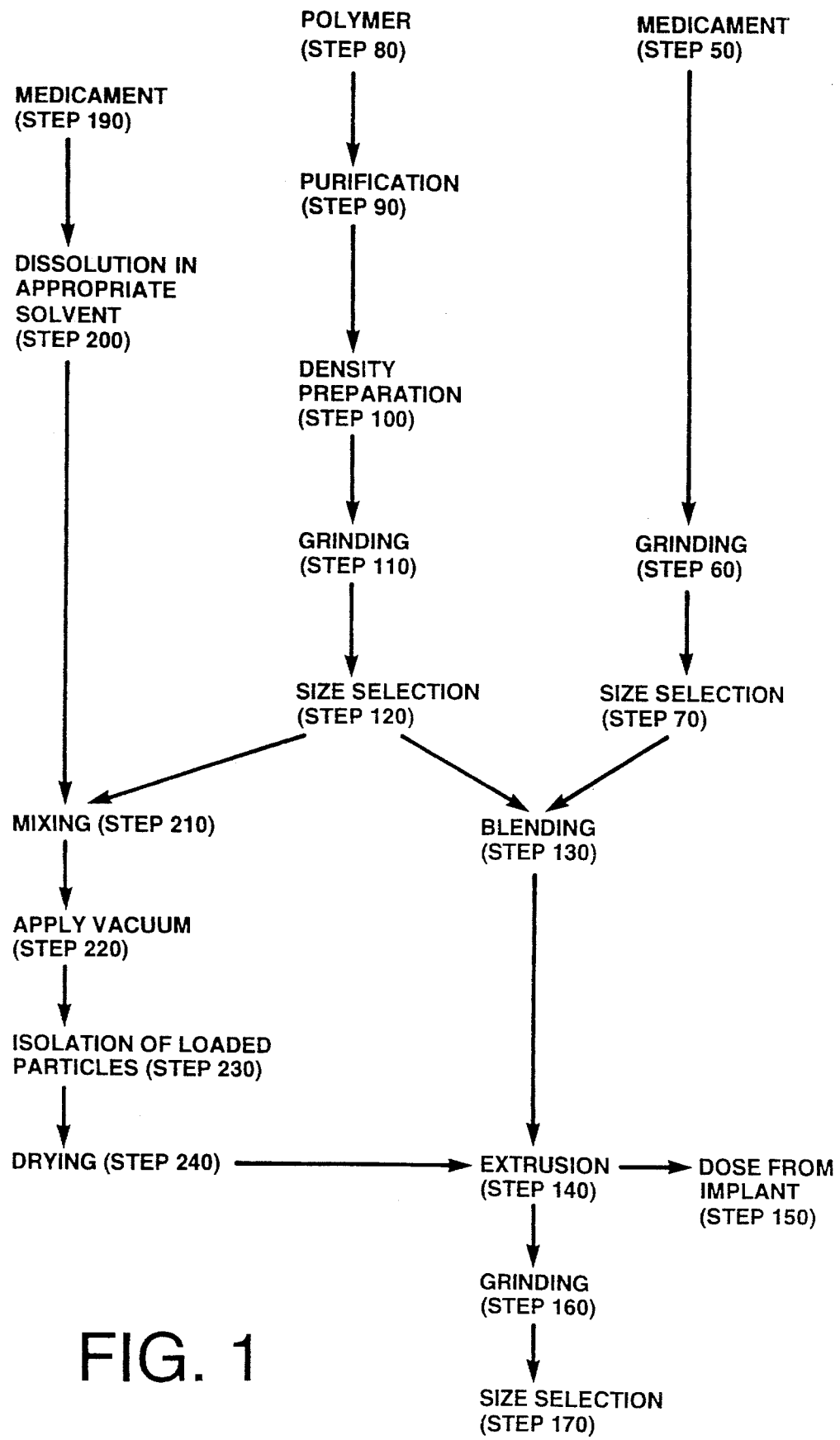
FIG. 1 is a flowchart disclosing the steps of formulating a bioerodible material of the invention.

Referring to FIG. 1, an embodiment of a method of the invention for the formulation of a medicament in a bioerodible material is depicted as a flowchart.

The medicament which is to be used is received from the manufacturer (50) and is ground (60) until the drug particles have been reduced to a substantially homogeneous predetermined size. The drug particles are then separated (70) according to size, for example by standard sieving, and a predetermined drug particle size (typically 5–15 microns) selected for use.

The polymer, as received from the manufacturer (80) is purified (90) to remove unreacted monomers, low molecular weight polymer and debris (such as the catalyst used in the polymer synthesis). The purification method is determined by the polymer being used and purification may not be necessary with sufficiently pure polymers.

In an exemplary embodiment, for example, to purify the polymer poly(lactide-co-glycolide) or poly(lactic-co-glycolic acid) (PLGA) so as to remove any residual lactide, glycolide or short chain oligomers, the technique referred to as solvent insolubility may be used. This technique requires dissolving the polymer in a first solvent and mixing the resulting solution with a second solvent in which the polymer is insoluble but with which the first solvent is miscible. As the polymer precipitates out of solution, it is collected (for example on a stirring rod), air dried, and then vacuum dried.

The purified polymer is then processed to achieve a predetermined density (100). In one embodiment, the density of the polymer is adjusted by the technique of solvent insolubility discussed above. In another embodiment, density adjustment is performed by dissolving the purified polymer in a solvent and vacuum drying or lyophilizing the resulting solution. By varying the ratio of polymer to solvent, the density of the resulting dried polymer may be varied.

It should be noted that although polymer purification and density adjustment are described as separate steps in this embodiment, another embodiment is possible in which the step polymer purification by the technique of solvent insolubility as described above is used for controlling polymer density. If further reduction of densities is required an additional density adjustment step may be performed.

Figure 2:
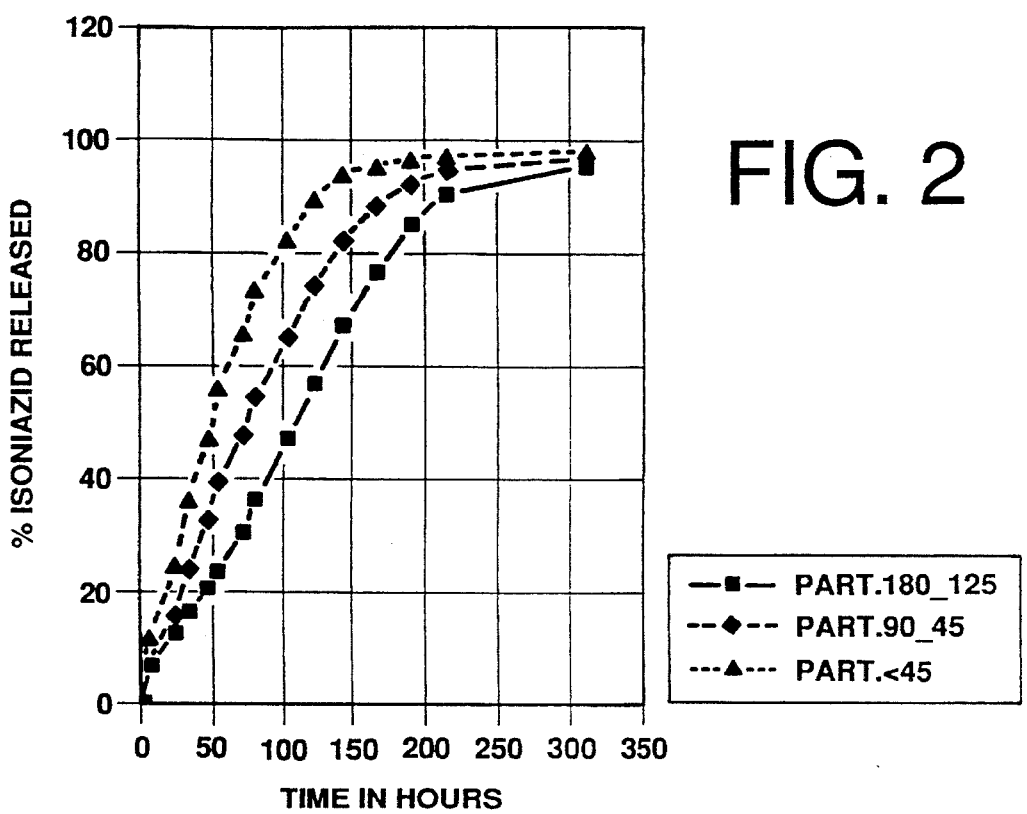
FIG. 2 is a set of graphs depicting the relationship of the release rate of a medicament as a function of time for implants made from various ranges of particle size of polymer.

The resulting polymer of the required density is cryogenically ground (110) until the polymer particles have been reduced to a substantially homogeneous predetermined size. The cryogenic cooling makes the polymer brittle and therefore easily ground to a predetermined size of particle. The polymer particles are then separated (120) according to size, for example by sieving, and a predetermined polymer particle size selected for use. The particles typically range in size from <10 μm to approximately 200 μm and different particle sizes are suitable for different applications. As is depicted in FIG. 2 (for the drug isoniazid in the polymer PLGA), the smaller the polymer particle size, the more rapid is the release of medicament.

The selected polymer particles and selected drug particles are dry blended (130) together to homogeneity at a predetermined ratio of drug to polymer.

In an alternative embodiment, medicament may be loaded into the pores of the polymer particles using a vacuum. In an exemplary embodiment illustrated in FIG. 1, a medicament (190) may be dissolved in an appropriate solvent (200). Preferably, the solvent will be water in which the polymer is insoluble. However, other solvents, such as ethanol, which will dissolve the medicament but not the polymer, may also be used. The chosen solvent must be capable of completely dissolving the medicament, but must not dissolve or substantially affect the polymer particles or their pore structure morphology.

Polymer particles prepared as described above (120) are added to the medicament solution and mixed (210). To ensure that the voids in the polymer particles are completely filled, vacuum is applied to the mixture (220) to remove trapped air from the particles. Several applications of vacuum of approximately 10–50 Torr may be necessary to completely remove all the air trapped within the porous structure of the polymer particles. The loaded particles are then isolated from the bulk medicament solution (230) by filtration or decanting to remove any excess solution, and then freeze dried or vacuum dried (240) to remove solvent from within the pores.

The blended mixture from either step 130 or 240 is then placed in an extrusion device and extruded (140) into a rod. In one embodiment the extrusion device is a high pressure ram extruder which has a controllable extrusion temperature. As illustrated in FIG. 1, the resulting extruded rod may then be used as an implant (150).

Figure 3:
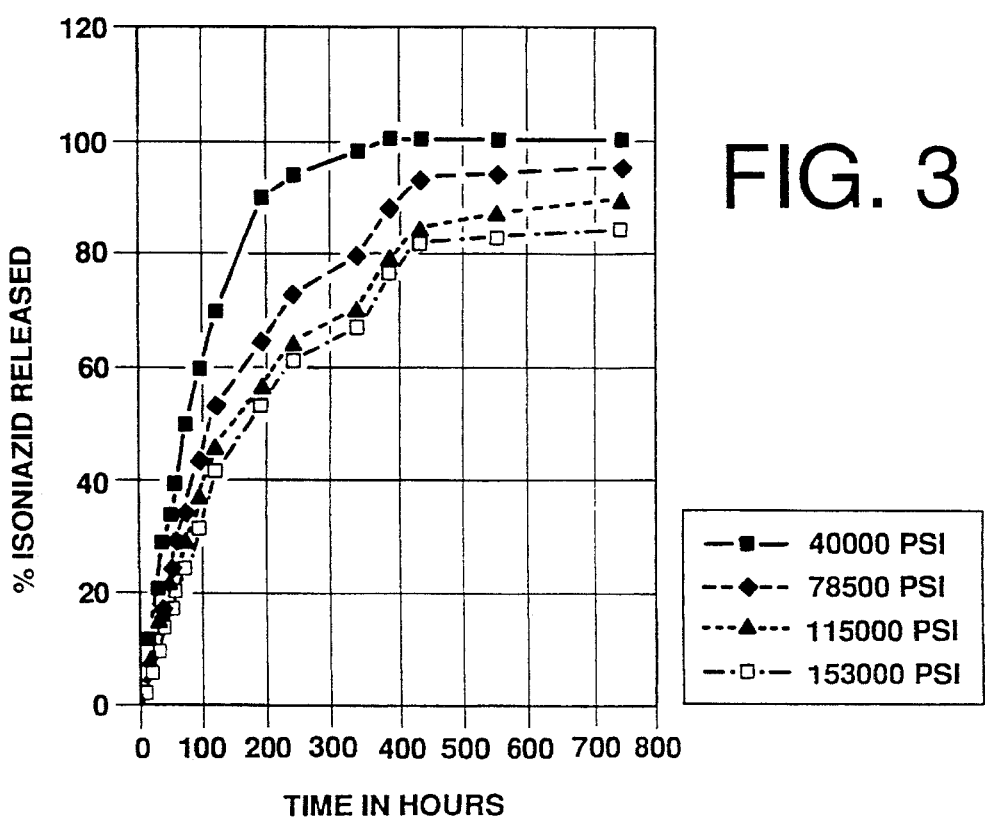
FIG. 3 is a set of graphs depicting the relationship of the release rate of a medicament as a function of time for implants made at different extrusion pressures.

As shown in FIG. 3 (for the drug isoniazid in the polymer PLGA), the higher the pressure of extrusion, the slower the release of medicament. The initial release rates (expressed as the slopes of the linear portion of the release profiles) diminish with increasing pressure and approach a limiting value at high pressure. Therefore, one skilled in the art may modify and control release rates by adjusting the extrusion pressure.

Figure 4:
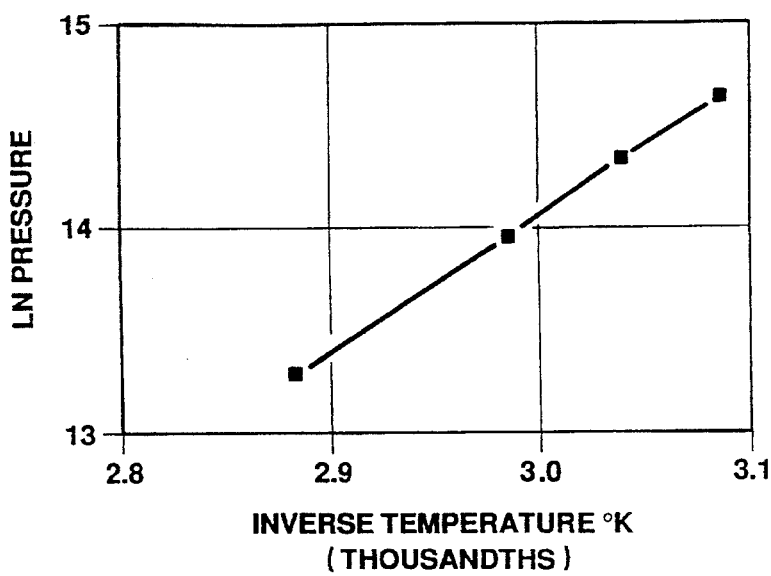
FIG. 4 is a graph of the natural logarithm of extrusion pressure versus inverse temperature.

It should be noted that higher pressures and especially lower temperatures are also suitable and that for the extrusion of a biological, temperatures less than 37° C. may be desired. This is because the application of pressure generates heat which may be especially detrimental to biologicals. Thus it is possible to cool the polymer/medicament mixture to avoid the problems of heat generation provided that the extruder used is capable of generating the pressures necessary to extrude the cooled mixture. A correlation between the pressure required for extrusion and temperature of the mixture is found to follow a ln (P) versus 1/T (°K) relationship (FIG. 4), with the various constants depending on such variables as polymer molecular weight, medicament molecular weight, lactide to glycolide ratio, ratio of medicament to polymer, etc.

The relationship between pressure and temperature may be expressed as:

$$\ln P = \ln(8lv/r^2) + \ln A + (\Delta E_v/R)T^{-1}$$

where l is the length of the tube extruded, v is the linear flow velocity, r is the tube radius, A is a preexponential constant, $\Delta E_v$ is the activation energy for viscous flow, and R is the universal gas constant. Thus, lower extrusion temperatures may be permitted by a corresponding increase in pressure.

In an embodiment which is an alternative to rod implantation, shown in FIG. 1, the extruded rod is then ground (160) and a predetermined particle size selected (170) for use as a powder (180), for example for inhalation use or hypodermic injection. In such an embodiment, the final particle size for injection or inhalation determines, to some extent, the initial particle size prior to extrusion. This is because, in order to obtain particles which all have the same ratio of medicament to polymer, it is necessary to use polymer and medicament particles for extrusion which are smaller than the final particle size desired.

For example, if it is desired to inject a sustained release tetanus toxoid into a newborn infant through a 25 gauge hypodermic needle, it is necessary that the particle size being injected be less than 10μ. For this size particle to have a consistent ratio of polymer to toxoid, it is necessary to grind the toxoid to about 1μ and blend it with PLGA particles which are less than 10μ. This mixture, when extruded into a rod at an extrusion temperature of 37° C. or less and again cryogenically ground to less than 10μ, will produce 10μ particles which are uniform in their ratio of polymer to toxoid. Conversely, if the tetanus toxoid particle is for injection into an adult (typically using an 18 gauge hypodermic needle) a final particle size of 50–125μ is acceptable with a corresponding increase in toxoid and polymer particle size possible.

EXAMPLE OF RELEASE OF A DRUG

One proposed use for a bioerodible implant produced by the method of the invention is for the treatment of tuberculosis with the drug isoniazid (isonicotinic acid hydrazide) in a bioerodible matrix of poly-(lactic-co-glycolic-acid), a copolymer of lactic and glycolic acids at a ratio of 75:25 (PLGA-75:25). The treatment of tuberculosis with this drug is especially suitable for use in a bioerodible implant. This is because the drug's regimen typically consists of the ingestion of daily doses of between 500 and 1000 mg of the drug for a period of three to six months. Thus a sustained release method of dispensing this drug would reduce the risk that the patient would not complete the entire course of treatment. In the following description of an embodiment of the method of formulating an implant for the release of a drug, the drug isoniazid in PLGA-75:25 is used for exemplary purposes, but other drugs and polymers may be used with the method as described.

Isoniazid as received from the manufacturer is ground in a ball mill containing ceramic balls until the drug crystals have been reduced to a substantially homogeneous size of between 5 and 10 microns.

The PLGA is purified by slowly adding a volume of a solution of the polymer PLGA dissolved in methylene chloride, tetrahydrofuran or, preferably, acetone at about 5% weight to volume of polymer to about 20 volumes of isopropanol under continuous stirring. The purified polymer, which precipitates from the isopropanol, is recovered on a stirring rod, as a fibrous, porous, "cocoon" which is then air dried to remove any solvent. Although typically less than 15 ppm solvent remains after air drying, this residual solvent is then reduced by vacuum drying to less than 5 ppm.

To adjust the density of PLGA, the solid polymer of PLGA-75:25 having a density of 1.22 gm/cm$^3$ is dissolved in the solvent such as methylene chloride, tetrahydrofuran, or, preferably, acetone. Since the ratio of the amount of solid polymer to solvent determines the final density of the polymer upon reconstitution, in order to obtain two different final polymer densities of about 0.8 gm/cm$^3$ and about 0.5 gm/cm$^3$, 7 gms and 3.5 gms of PLGA-75:25 are dissolved respectively in 70 ml of methylene chloride, or acetone. Each of the resulting solutions are respectively placed in a rotary-vacuum apparatus (such as a BUCHI Rotorvapor®, BUCHI Laboratoriums-Technik AG, Flawilschweij, Switzerland) refrigerated by dry ice and vacuum dried into a film. Each of the resulting films are then further dried in a desiccator for between one and two days, after which time substantially none of the solvent methylene chloride remains.

Each of the different density individual polymer films is then cryogenically ground, for example in a TEKMAR A-10 Analytical Mill (manufactured by the Tekmar Co., Cincinnati, Ohio) with a C-10 adaptor containing liquid nitrogen and sieved to isolate particles of the size 45–90 microns.

Each of the ground polymer particles of different densities is respectively mixed with the prepared isoniazid particles to form mixtures which are, for example, 25% by weight isoniazid. Each of the mixtures of different densities PLGA and isoniazid is respectively extruded in a ram extruder (for example a Compac Type MPC 40-1 extruder made by Stenhoj Co., Denmark) at 40000 psi at between 70° C. and 74° C. into a form suitable for implantation.

Figure 5:
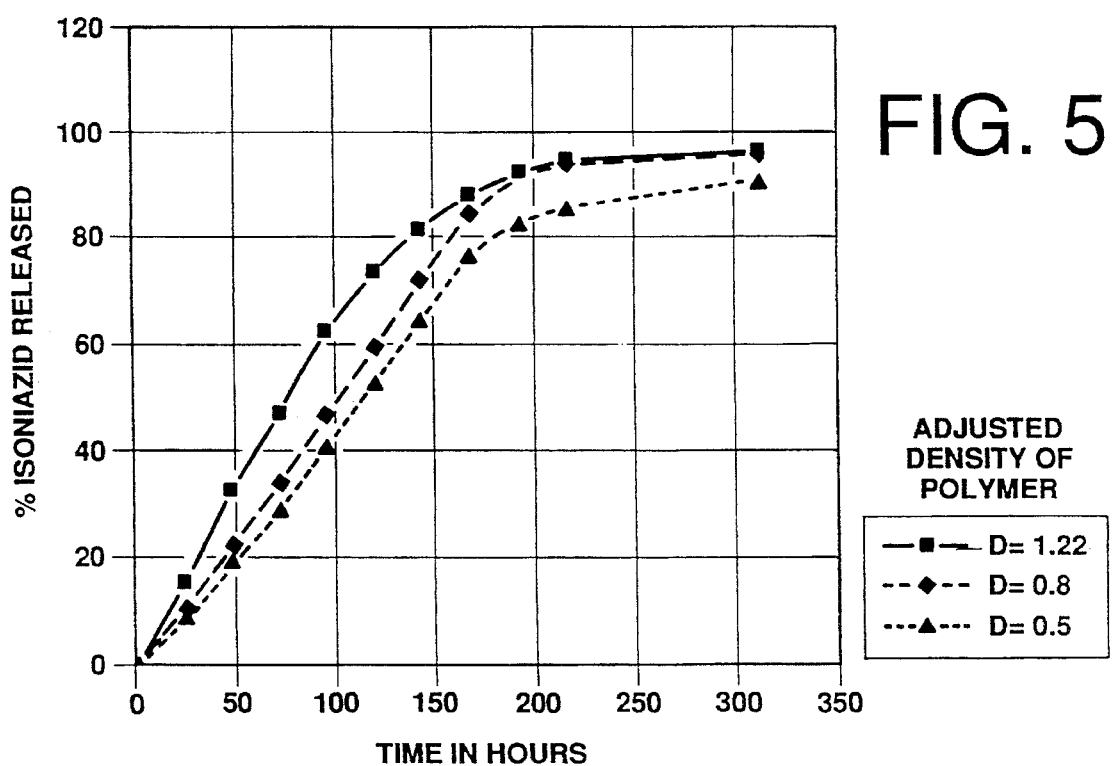
FIG. 5 is a set of graphs depicting the relationship of the release rate of a medicament as a function of time for implants made according to the embodiment of the method of the invention depicted in FIG. 1.

The result of an in vitro measurement of the release of isoniazid as a function of time can be seen in FIG. 5. FIG. 5 demonstrates that the rate of release of isoniazid depends upon the density of the polymer particles from which the implant is extruded and hence control of the polymer particle density may be used to control the rate at which the drug is dispensed.

The technique of dry-blending polymer and medicament without the use of a solvent in which to dissolve the polymer may be used in conjunction with control of the polymer particle size to achieve control of release rates. Polymer in the form of extrudate received from the supplier or in the form of purified fibrous precipitate, or prepared as foam may be ground and sieved to retain specific particle size ranges. These may then be blended with micron-sized medicament in a rotary blender, or by any means capable of achieving a homogeneous mixture. In the blending process both polymer and medicament may be mixed as dry powders.

Polymer as received from the supplier was directly ground without first preparing a foam. The polymer, a PLGA-75:25, was ground at liquid nitrogen temperatures using a Tekmar A-10 mill equipped with a liquid nitrogen reservoir. The ground polymer was sieved through a series of Taylor screens (45, 90, 125, and 180 microns) and the following particle size ranges were isolated: <45, 45–90, and 125–180 microns. The isoniazid (INH) medicament was ground to a maximum particle size of 20 microns with 75% of the particles in the range 5–10 microns. The ground polymer fractions were blended with the dry micronized INH powder to form mixtures containing 25% by weight of INH. The blend was extruded as described previously at 40,000 psi through a 1.0 mm diameter cylindrical die in the temperature range 68°–82° C., depending on the polymer particle size. The extruded rods were cut into convenient size for in vitro measurement of release.

Release of INH from the extruded matrices described above was measured in phosphate buffered saline (PBS) at 37° C. FIG. 2 shows release profiles for the matrices formed from the 3 PLGA size ranges. Thus, it is seen that release rates may be altered by a factor of greater than two-fold by reduction of the polymer particle size from 125–180 microns to less than 45 microns.

In an alternative embodiment, the medicament may be loaded into the polymer particles by preparing a slurry of polymer particles in a solution of medicament and applying a vacuum to fill the voids of the particles. This result may be accomplished by dissolving the drug without dissolving or causing swelling or other morphological changes in the polymer. Preferably, the solvent should have a high vapor pressure so that it may easily be removed by volatilization or sublimation. The drug solution is then added to the foam, which itself may be ground to a particular particle size range, to form a slurry. In order to force the drug into the pore structure, the slurry is degassed, either as a liquid/solid mixture or after freezing. This process effectively removes air from the pores. After degassing, the slurry, if frozen, is thawed so that the drug solvent melts and air, or any other suitable gas, is allowed to enter the system at any desired pressure. The gas pressure forces the drug solution into the pores. The mixture is then re-frozen and the solvent is then removed by lyophilization, a process which traps the drug within the pores.

In one embodiment illustrating the control of polymer foam density, PLGA-85:15 was dissolved in benzene to form solutions of concentrations 50, 100, and 200 mg/ml. After freeze drying, bulk densities were measured yielding values of 0.11, 0.17, and 0.27 grams/cm$^3$ respectively.

In a second embodiment, low bulk density foam was loaded with the narcotic antagonist naltrexone. Porous PLGA-85:15 was prepared by freeze drying a benzene solution containing 132 mg/ml of the polymer. The resulting bulk density was 0.24 gr/cm$^3$. Samples were then immersed in solutions of naltrexone in methanol containing either 0.12 or 0.25 gr/cm$^3$, and degassed several times as described to force the solution into the porous polymer. After evaporating the methanol, the weight fraction of naltrexone was determined gravimetrically and compared to expected values calculated as shown below. Results were as follows:

| | | |
|---|---|---|
| Concentration of naltrexone (gr/cm$^3$): | 0.12 | 0.25 |
| PLGA-85:15 density (gr/cm$^3$) | 0.26 | 0.24 |
| % naltrexone in foam (experimental) | 29.1 | 57.1 |
| % naltrexone in foam (calculated) | 26.9 | 45.5 |

The weight fraction of medicament loaded into the pores of the polymer particles may be calculated using the following equation:

$$f = \left[ 1 + \frac{d_b d_m}{C(d_m - d_b)} \right]^{-1}$$

where $f$ = the weight fraction of medicament in the polymer particle foam;

$C$ = the concentration of medicament in the solution;

$d_b$ = the bulk density of the polymer particle foam; and $d_m$ = the absolute density of the polymer.

The bulk density of the foam ($d_b$) is defined as the weight of the foam per overall unit volume and includes all void volume incorporated within the unit volume. The absolute density of the polymer ($d_m$) is the weight of the polymer per unit volume. Thus, the difference between the two values represents the volume of the void which becomes filled with the medicament solution. The assumptions upon which this calculation is based are that the void volume is completely occupied by the medicament solution, no change in volume occurs on exposure of the foam to the medicament solution, and that all medicament is trapped within the foam by lyophilization.

This method of loading medicament into the polymer particles provides several advantages. The method is especially useful in that foams of any desired density may be produced in advance and stored until needed. In addition, the user may specify a desired weight fraction of medicament in the polymer, and calculate the bulk or absolute foam densities that will be required to load a given solution of medicament. The method is compatible with any water- or ethanol-soluble medicament, or with any solvent in which the medicament is soluble, but which leaves the polymer substantially unchanged. The method requires that an excess of medicament solution be used, but excess medicament which is not entrapped in the foam may be recovered by lyophilization and reused.

EXAMPLE OF RELEASE OF A BIOLOGICAL

Another proposed use for a bioerodible implant produced by the method of the invention is for the treatment of advanced adenocarcinoma of the prostate with analogs of the biological LHRH (Luteinizing Hormone-Releasing Hormone) again in a bioerodible matrix of PLGA-75:25. The treatment of advanced prostate cancer with LHRH reduces the level of the hormone testosterone which in turn has a palliative effect on the disease. Presently a reduction in testosterone level may be brought about by implantation of conventional solvent based microcapsulation or matrix formulation of LHRH analogs or other drugs, or by the surgical technique of bilateral orchiectomy.

The treatment of advanced prostate cancer with LHRH in a bioerodible implant is especially desirable because it avoids the psychological ramifications attendant with an orchiectomy. In the following description of an embodiment of the method of formulating an implant with a biological, the LHRH analog, (des-gly$^{10}$)-(D-Trp$^6$,Pro$^9$)-LHRH ethylamide (LNRH-An), in PLGA-75:25 is used for exemplary purposes, but other biologicals and polymers may be used with the method as described.

In this embodiment, the LHRH-An is used as received from the manufacturer without purification. The LHRH-An was ground in a mortar with pestle until, as verified by microscopic analysis, all particles were less than 20μ, with the large majority being between 5–15 microns.

For the purposes of this example, two PLGA's, having lactide to glycolide ratios of 90:10 and 75:25, are used. Each polymer is purified, using the technique of solvent insolubility discussed above, by dissolving the polymer as received from the manufacturer in acetone to form a solution at a concentration of 0.05 grams/ml. One volume of this solution is slowly added with stirring to about ten volumes of isopropanol. The purified polymer "cocoons" which form are on dried for one day and then vacuum dried over desiccant for two to seven days. This purification step is sufficient to reduce the specific gravity of each of the polymers from 1.33 to 1.19 and the purified polymers are then used in this example with no further reduction in density.

Each adjusted density purified polymer is cryogenically ground for 6–10 minutes at 20,000 rpm in a TEKMAR A-10 Analytical Mill (manufactured by the Tekmar Co., Cincinnati, Ohio) with a C-10 adapter containing liquid nitrogen. Alternatively the same result may be achieved by water cooling the mill and grinding the polymer in pulses of 30 seconds to one minute, with intervening intervals of 5–10 minutes allowed for cooling the polymer. The ground polymers were then sieved to isolate particles of the size 45–90 microns.

The ground polymer particles are milled together with LHRH-An particles for 24 hours without grinding agents to insure efficient blending without further particle size reduction. The ratio of LHRH-An to polymer is such as to form a 2.9% by weight mixture. The mixture is extruded using a Compac type MPC 40-1 hydraulic press which maintains a constant temperature by means of external heating tapes on the mold and constant pressure control on the drug/polymer mixture. Extrusions are performed at 68–71 degree C. at 16,800 psi to yield extruded cylindrical forms suitable for implantation. The extruded cylinders are then reground and sieved to isolate the following size range 45–90, 90–125 and 125–180 microns, suitable for injection.

In vitro release studies indicate a dependence of rates of release on polymer composition, but relatively little dependent on matrix particle size. Release rates, computed from the linear portion of the cumulative fraction release versus time curves, for the six formulations a shown in Table 1.

In vivo tests were conducted to determine the efficacy of these formulations in reducing serum testosterone. In these tests, Sprague-Dawley rats (mean weight 380±9 g.) each received a subcutaneous injection of 102 mg of ground matrix to deliver a mean dose of 3.0 mg of LHRH-An (7.8 mg/kg). The serum testosterone levels as measured by radioimmunoassay fell from a mean of 3.58±1.26 ng/ml for controls to 0.79±0.29 ng/ml for all experimental groups for the time period of day 6 to day 124 post injection. This represents a significant reduction in testosterone levels of 77.9%.

Still another proposed use for a bioerodible implant produced by the method of the invention is for treatment cancer and AIDS with the T-cell growth factor Interleukin-2 (IL-2). Although Interleukin-2 is an extremely heat-labile molecule, the controlled pressure and temperature method of the invention permits the fabrication of a bioerodible rod containing IL-2 such that functional IL-2 is released from the implanted rod over a period of eleven days. Thus the method of the invention may not only be used with drugs or smaller biologicals, but it can also be used with biologicals whose exposure to the heat generated by the pressure applied during rod fabrication would otherwise be damaging.

Having showed the preferred embodiments, those skilled in the art will realize many variations are possible which will still be within the spirit and scope of the claimed invention. Therefore, it is the intention to limit the invention only as indicated by the scope of the claims.

TABLE 1

RELEASE RATE VERSUS PARTICLE SIZE AND POLYMER COMPOSITION

| Matrix Particle size, micron | Polymer composition | Release rate $hr^{-1}$ |
|---|---|---|
| 45–90 | 75:25 | 0.0015 |
| 90–125 | 75:25 | 0.0013 |
| 125–180 | 75:25 | 0.0014 |
| 45–90 | 90:10 | 0.0025 |
| 90–125 | 90:10 | 0.0027 |
| 125–180 | 90:10 | 0.0019 |

We claim:

1. A method for forming a bioerodible sustained time release particle for the continuous release of a medicament, said method comprising the steps of:

selecting a medicament for use;

selecting a bioerodible polymer PLGA for use;

adjusting the density of the bioerodible polymer PLGA;

grinding and sorting the density adjusted bioerodible polymer PLGA to select density adjusted bioerodible polymer PLGA particles of a predetermined size, said particles having pores;

dissolving the medicament in a solvent in which the bioerodible polymer PLGA is not soluble to form a medicament solution;

mixing the selected density adjusted bioerodible polymer PLGA particles into said solution of the medicament;

applying a vacuum to the suspension of said solution of medicament and density adjusted bioerodible polymer PLGA particles to remove air from said pores of said density adjusted bioerodible polymer PLGA;

releasing said vacuum to load said solution of medicament into said particles; and isolating the density adjusted bioerodible polymer PLGA particles which are loaded with said medicament.

2. The method of claim 1 wherein said medicament is a drug.

3. The method of claim 1 wherein said medicament is a biological.

4. The method of claim 1 wherein said steps take place at a temperature of less than 37 degrees centigrade.

5. The method of claim 1 wherein said step of adjusting the density of the bioerodible polymer PLGA comprises the steps of:

dissolving the bioerodible polymer PLGA in a solvent in a ratio sufficient to produce a desired density when the polymer is reconstituted; and evaporating the solvent to recover the reconstituted polymer.

6. The method of claim 5 wherein the step of evaporating the solvent to recover the reconstituted polymer comprises the step of vacuum drying.

7. The method of claim 1 wherein prior to the step of adjusting the density of the bioerodible polymer PLGA, said polymer is purified.

8. The method of claim 1 wherein said step of processing the density adjusted bioerodible polymer PLGA to form particles of a predetermined size comprises the step of grinding and separating the particles of polymer into predetermined sizes.

9. The method of claim 8 wherein the step of separating the particles of polymer comprises the step of sieving.

10. A method for forming a biodegradable matrix suitable for use in a sustained time release particle, said method comprising the steps of:

selecting a bioerodible polymer PLGA for use;

adjusting the density of the bioerodible polymer PLGA; and grinding and sorting the density adjusted bioerodible polymer PLGA to select density adjusted bioerodible polymer PLGA particles of a predetermined size, wherein said density adjusted bioerodible polymer PLGA particles are bioerodible at a rate which is determined by said adjusted density and said predetermined size.

11. A sustained time release particle for the release of a medicament made by a method comprising the steps of:

selecting a medicament for use;

selecting a bioerodible polymer PLGA for use;

adjusting the density of the bioerodible polymer PLGA;

grinding and sorting the density adjusted bioerodible polymer PLGA to select density adjusted bioerodible polymer PLGA particles of a predetermined size, said particles having pores;

dissolving the medicament in a solvent in which the bioerodible polymer PLGA is not soluble to form a medicament solution;

mixing the selected density adjusted bioerodible polymer PLGA particles into said solution of the medicament;

applying a vacuum to the suspension of said solution of medicament and density adjusted bioerodible PLGA polymer particles to remove air from said pores of said density adjusted bioerodible polymer PLGA;

releasing said vacuum to load said solution of medicament into said particles; and isolating the density adjusted bioerodible polymer PLGA particles which are loaded with said medicament.

12. A method for forming a bioerodible sustained time release material for the continuous release of a medicament, said method comprising the steps of:

selecting a medicament in solid form for use;

selecting a bioerodible polymer PLGA for use;

adjusting the density of the bioerodible polymer PLGA;

grinding and sorting the density adjusted bioerodible polymer PLGA to select density adjusted bioerodible polymer PLGA particles of a predetermined size;

mixing said medicament in solid form and said selected density adjusted bioerodible polymer PLGA particles; and extruding said mixture of medicament-loaded selected density adjusted bioerodible polymer PLGA into a rod using a predetermined temperature and pressure, wherein said density adjusted bioerodible polymer PLGA rod is bioerodible at a rate which is determined by said adjusted density and said predetermined size of said selected density adjusted bioerodible polymer PLGA particles.

13. The method of claim 12 wherein said medicament is a drug.

14. The method of claim 12 wherein said medicament is a biological.

15. The method of claim 12 wherein said steps take place at a temperature of less than 37 degrees centigrade.

16. The method of claim 12 wherein said step of adjusting the density of the bioerodible polymer comprises the steps of:

dissolving the bioerodible polymer in a solvent in a ratio sufficient to produce a desired density when the polymer is reconstituted; and removing the solvent to recover the reconstituted polymer.

17. The method of claim 12 wherein prior to the step of adjusting the density of the bioerodible polymer, said polymer is purified.

18. The method of claim 12 wherein the step of grinding and sorting the particles of polymer comprises the step of sieving.

19. The method of claim 12 wherein subsequent to said extrusion said rod is ground to particles of a predetermined size.

20. A bioerodible sustained time release material for the continuous release of a medicament formed from a method comprising the steps of:

selecting a medicament in solid form for use;

selecting a bioerodible polymer PLGA for use;

adjusting the density of the bioerodible polymer PLGA;

grinding and sorting the density adjusted bioerodible polymer PLGA to select density adjusted bioerodible polymer PLGA particles of a predetermined size;

mixing said medicament in solid form and said selected density adjusted bioerodible polymer PLGA to produce a medicament-loaded selected density adjusted bioerodible polymer PLGA; and extruding said mixture of medicament-loaded selected density adjusted bioerodible polymer PLGA into a rod using a predetermined temperature and pressure, wherein said density adjusted bioerodible polymer PLGA rod is bioerodable at a rate which is determined by said adjusted density and said predetermined size of said selected density adjusted bioerodible polymer PLGA particles.

21. The method of claim 5, wherein said density adjustment step produces a bioerodible polymer PLGA with density of from approximately 0.11 to approximately 1.22 $g/cm^3$.

22. The method of claim 21 including wherein said density adjustment step includes producing a solution of from approximately 0.05 to approximately 0.1 grams PLGA per milliliter solvent.

23. The method of claim 21, wherein said density adjustment step produces a bioerodible polymer PLGA with density of approximately 0.5 $g/cm^3$.

24. The method of claim 21, wherein said density adjustment step produces a bioerodible polymer PLGA with density of approximately 0.8 $g/cm^3$.

25. The method of claim 16, wherein said density adjustment step produces a bioerodible polymer PLGA with density of from approximately 0.11 to approximately 1.22 $g/cm^3$.

26. The method of claim 25 wherein said density adjustment step includes producing a solution of from approximately 0.05 to approximately 0.1 grams PLGA per milliliter solvent.

27. The method of claim 25, wherein said density adjustment step produces a bioerodible polymer PLGA with density of approximately 0.5 $g/cm^3$.

28. The method of claim 25, wherein said density adjustment step produces a bioerodible polymer PLGA with density of approximately 0.8 $g/cm^3$.

29. The method of claim 10, wherein said density adjustment step further includes the steps of:

dissolving said bioerodible polymer PLGA in a solvent to form a polymer solution; and freeze drying said polymer solution to form a film of a predetermined density.

30. The method of claim 10, wherein said density adjustment step further includes the steps of:

dissolving said bioerodible polymer PLGA in a solvent to form a polymer solution; and precipitating said bioerodible polymer PLGA from said polymer solution in a liquid which is miscible with said solvent but in which said bioerodible polymer PLGA is insoluble to form a precipitate of a predetermined density.

31. The method of claim 1, further including the step of extruding the density-adjusted bioerodible polymer PLGA loaded with medicament into a rod using a predetermined temperature and pressure.

32. The method of claim 31 wherein subsequent to said extrusion said rod is ground to particles of a predetermined size.

* * * * *